US008639013B2

(12) United States Patent
Kenny

(10) Patent No.: US 8,639,013 B2
(45) Date of Patent: Jan. 28, 2014

(54) SYSTEM AND METHODS FOR GENERATING A BRIGHTFIELD IMAGE USING FLUORESCENT IMAGES

(75) Inventor: Kevin Bernard Kenny, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 326 days.

(21) Appl. No.: 13/211,725

(22) Filed: Aug. 17, 2011

(65) Prior Publication Data
US 2013/0044933 A1 Feb. 21, 2013

(51) Int. Cl.
*G06K 9/00* (2006.01)
(52) U.S. Cl.
USPC .......................................... 382/133; 382/162
(58) Field of Classification Search
USPC ........................................................ 382/133
See application file for complete search history.

(56) References Cited

U.S. PATENT DOCUMENTS

| | | | |
|---|---|---|---|
| 7,483,554 B2 | 1/2009 | Kotsianti et al. | |
| 7,741,045 B2 | 6/2010 | Gerdes et al. | |
| 2001/0017938 A1* | 8/2001 | Kerschmann et al. | 382/133 |
| 2004/0223910 A1 | 11/2004 | Kiselev et al. | |
| 2008/0031521 A1 | 2/2008 | Cline et al. | |
| 2008/0032321 A1 | 2/2008 | Cline et al. | |
| 2008/0032328 A1 | 2/2008 | Cline et al. | |
| 2008/0033657 A1 | 2/2008 | Cline et al. | |
| 2011/0074944 A1 | 3/2011 | Can et al. | |
| 2012/0200694 A1* | 8/2012 | Garsha et al. | 348/79 |

FOREIGN PATENT DOCUMENTS

| | | |
|---|---|---|
| GB | 2434651 A | 1/2007 |
| WO | 9855026 A1 | 12/1998 |
| WO | WO2008021677 A2 | 2/2008 |
| WO | WO2008021681 A2 | 2/2008 |

OTHER PUBLICATIONS

Search Report and Written Opinion from corresponding PCT Application No. PCT/EP2012/065943 dated Nov. 13, 2012.
Tang, "Ultraviolet-Visible Acousto-Optic Tunable Spectroscopic Imager for Medical Diagnosis", Journal of Biomedical Optics, vol. 3, No. 1, pp. 80-84, Jan. 1, 1998.
Aleksandra et al., "The possibilities of improvement the sensitivity of cancer fluorescence diagnostics by computer image processing", vol. 6859, pp. 68591E-68591E-8, Jan. 1, 2008.
Stehle et al., "Enhancement of visual contrast in fluorescence endoscopy", pp. 537-540, Jun. 23, 2008.
Xia et al., "Color image enhancement algorithm based on logarithmic transform coefficient histogram", pp. 78700Y-78700Y-10, Jan. 1, 2011.

(Continued)

*Primary Examiner* — Amir Alavi
*Assistant Examiner* — Kenny Cese
(74) *Attorney, Agent, or Firm* — Eileen W. Gallagher

(57) ABSTRACT

A method for generating a brightfield type image, which resembles a brightfield staining protocol of a biological sample, using fluorescent images is provided. The steps comprise acquiring two or more fluorescent images of a fixed area on a biological sample, mapping said fluorescent image into a brightfield color space, generating a brightfield image, and optionally applying a sharpening transformation correction. Also provided is an image analysis system for generating a brightfield type image of a biological sample using fluorescent images.

18 Claims, 3 Drawing Sheets

(56) References Cited

OTHER PUBLICATIONS

Bini et al., "Confocal mosaicing microscopy of human skin ex vivo: spectral analysis for digital staining to simulate histology-like appearance", Journal of Biomedical Optics, vol. 16, No. 7, pp. 076008-076008, Jul. 1, 2011.

Mansfield et al., "Visualization of Microscopy-Based Spectral Imaging Data From Multi-Label Tissue Sections", Current Protocols in Molecular Biology, pp. 14.19.1-14.19.15, Oct. 2008.

Buchynska et al., "Immunofluorescence Staining of Paraffin Sections: Creating Dab Staining Like Virtual Digital Images, Using Cmyk Color Conversion", Technical Advance, Experimental Oncology, vol. 30, vol. 4, pp. 327-329, 2008.

* cited by examiner

SYSTEM AND METHODS FOR GENERATING A BRIGHTFIELD IMAGE USING FLUORESCENT IMAGES

BACKGROUND

The invention relates generally to a method to map a set of biomarker images acquired by a fluorescent microscope into a new color space where the mapped image intensity values represent a brightfield modality.

In traditional histological staining with Hematoxylin & Eosin (H&E), the basophilic dye Hematoxylin (H) is used to stain the cell nuclei blue, and the acidophilic dye Eosin (E) is used as a counter-stain to stain cytoplasm, connective tissue (collagen), muscle fibers, connective tissue, and red blood cells. Eosin interacts with different cellular components in the tissue producing different shades of pink color based on charge properties of the molecules to which eosin are binding. Other chromogenic stains have been used for visualization in immunodiagnostics and assays, for example brown diaminobenzideine (DAB) staining is common.

Often cellular components can be alternatively labeled using molecular markers (dyes and antibodies) with fluorescent dyes. For example, cell nuclei can be stained with DAPI (a fluorescent dye that binds DNA specifically) while other regions in the tissue can be labeled immunofluorescently where the molecules of interest are targeted by directly conjugated antibodies, or by primary secondary amplification detection. For some structures, such as red blood cells (RBC), tissue autofluorescence captured by a set of filters can be used for detection. Fluorescent imaging modality has the advantage of capturing each of these tissue structures individually, hence enabling accurate localization and quantification.

However, histopathological diagnosis based on fluorescent images is not a common practice because fluorescent images do not provide structural and morphological details that are essential for pathologists to diagnose. Brightfield H&E staining, often combined with brown staining techniques, are also often favored as there is a large body of knowledge about these techniques, assembled for decades in pathology laboratories.

Methods to convert fluorescent images into a pseudo brightfield image are known. However, these methods typically reassign a specific color space (wavelength) to each fluorescent dye such that the fluorescent images are recolored into the brightfield space. These methods do not transpose the fluorescent images into an image that represents the image of the biological sample that would be obtained if the biological sample were subjected to a specified brightfield staining protocol, such as H&E. Also disclosed, in U.S. patent application Ser. No. 12/569,396 entitled "Systems and Methods for Generating a Brightfield Image Using Fluorescent Images" and filed on Sep. 29, 2009 is a method which creates a brightfield image from fluorescent images wherein structural features and details of the biological sample are identified as if the image was obtained directly from a specified brightfield staining protocol. The U.S. patent application is incorporated herein by reference.

However a need exist for enhancing contrast and identifying structural features such as cell boundaries. There also exists a need for improving the ability to distinguish and identify internal features such as nucleus, cell membrane and cytoplasm as these areas may lack full resolution. As such a virtual stained image (VSI) with improved acutance, such as edge contrast, is desired.

BRIEF DESCRIPTION

As noted, fluorescent markers were previously used alone to identify the nuclei, epithelium and stroma to provide information on the cell compartments. The methods combine the morphological function of fluorescent markers with the function of fluorescent biomarkers, which are used to identify the expression of proteins and pathways for disease in tissue based, in part, on cell morphology and biological pathways. The disclosed invention describes a method to map a set of biomarker and autofluorescence images acquired by a fluorescent microscope into a new color space where the mapped image intensity values represent a brightfield modality such as H&E staining.

In one embodiment, a method for generating a brightfield type image that resembles a brightfield staining protocol of a biological sample, using fluorescent images is provided for. The method comprising the steps of acquiring image data of two or more fluorescent images of a fixed area on a biological sample, analyzing the image data utilizing, at least in part, featured-based information or pixel intensity data information to generate mapping parameters wherein said mapping parameters comprises a nonlinear estimation model, applying said mapping parameters to the fluorescent images, transforming the two or more fluorescent imaging into a brightfield color space, generating a brightfield type image, and applying a sharpening transformation correction to the brightfield type image.

In another embodiment an image analysis system for generating a brightfield type image that resembles a brightfield staining protocol of a biological sample, using fluorescent images is provided. The system comprises a digital imaging device adapted to acquire two or more fluorescent images of a fixed area on a biological sample, and a processing device adapted to apply mapping parameters to transform the two or more fluorescent images into a brightfield type image including a sharpening transformation.

DRAWINGS

These and other features, aspects, and advantages of the present invention will become better understood when the following detailed description is read with reference to the accompanying drawings in which like characters represent like parts throughout the drawings, wherein.

Figure 3A:
Figure 3B:
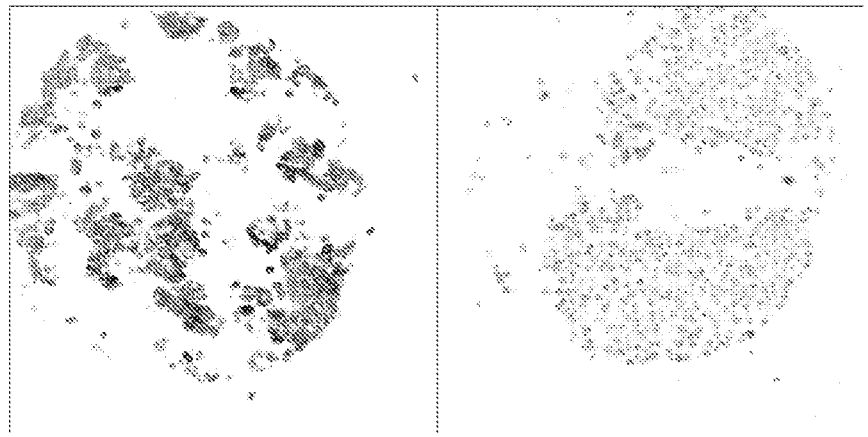
Figure 3C:
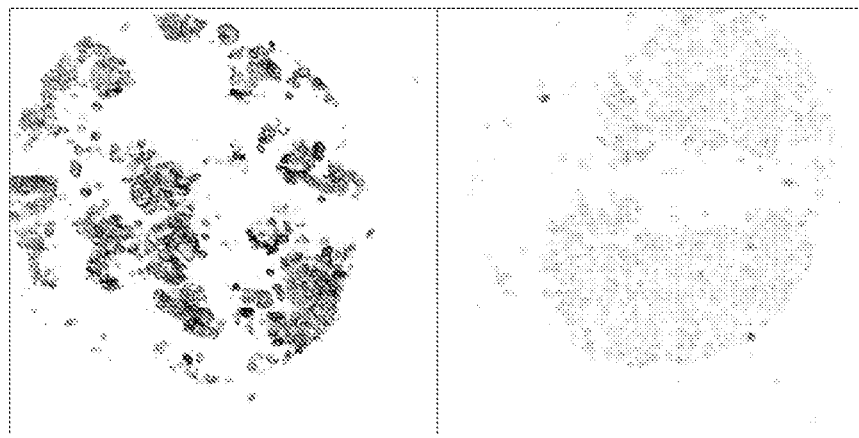

FIG. 3 shows a monochrome representation of the color VSI obtained by processing the fluorescence images according to the method taught herein. Image (a) represents the red channel; (b) represents the green channel; and (c) represents the blue channel. The cells in the field of view are obtained from the same pellets as the images in FIG. 1.

DETAILED DESCRIPTION

To more clearly and concisely describe and point out the subject matter of the claimed invention, the following definitions are provided for specific terms that are used in the following description and the claims appended hereto.

The term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab')2, or Fab'). In addition, aggregates, polymers, and conjugates of immunoglobulins or their fragments may be used where appropriate so long as binding affinity for a particular molecule is substantially maintained.

The term "binder" refers to a molecule that may bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, or haptens. A suitable binder may be selected depending on the sample to be analyzed and the targets available for detection. For example, a target in the sample may include a ligand and the binder may include a receptor or a target may include a receptor and the binder may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

The term "biological sample" refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions, and cells isolated from mammals including, humans. Biological samples also may include sections of the biological sample including tissues (e.g., sectional portions of an organ or tissue). Biological samples may also include extracts from a biological sample, for example, an antigen from a biological fluid (e.g., blood or urine).

A biological sample may be of prokaryotic origin or eukaryotic origin (e.g., insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee, or human).

The term "fluorophore" or "fluorescent signal generator" refers to a chemical compound, which when excited by exposure to a particular wavelength of light, emits light at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2, 2'disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl) phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)4-methylcoumarin, , 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, pyrelium dyes, and squaraines.

The term "in situ" generally refers to an event occurring in the original location, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

The term "probe" refers to an agent having a binder and a label, such as a signal generator or an enzyme. In some embodiments, the binder and the label (signal generator or the enzyme) are embodied in a single entity. The binder and the label may be attached directly (e.g., via a fluorescent molecule incorporated into the binder) or indirectly (e.g., through a linker, which may include a cleavage site) and applied to the biological sample in a single step. In alternative embodiments, the binder and the label are embodied in discrete entities (e.g., a primary antibody capable of binding a target and an enzyme or a signal generator-labeled secondary antibody capable of binding the primary antibody). When the binder and the label (signal generator or the enzyme) are separate entities they may be applied to a biological sample in a single step or multiple steps. The term "fluorescent probe" refers to an agent having a binder coupled to a fluorescent signal generator.

The term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal, or a radioactive signal. Examples of signal generators include one or more of a chromophore, a fluorophore, a Raman-active tag, or a radioactive label. As stated above, with regard to the probe, the signal generator and the binder may be present in a single entity (e.g., a target binding protein with a fluorescent label) in some embodiments. Alternatively, the binder and the signal generator may be discrete entities (e.g., a receptor protein and a labeled-antibody against that particular receptor protein) that associate with each other before or upon introduction to the sample.

The term "solid support" refers to an article on which targets present in the biological sample may be immobilized and subsequently detected by the methods disclosed herein. Targets may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

The term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant (KA) for the target no lower than about $10^5$ $M^{-1}$ under ambient conditions such as a pH of about 6 to about 8 and temperature ranging from about 0° C. to about 37° C.

The term "target," refers to the component of a biological sample that may be detected when present in the biological sample. The target may be any substance for which there exists a naturally occurring specific binder (e.g., an antibody), or for which a specific binder may be prepared (e.g., a small molecule binder or an aptamer). In general, a binder may bind to a target through one or more discrete chemical moieties of the target or a three-dimensional structural component of the target (e.g., 3D structures resulting from peptide folding). The target may include one or more of natural or modified peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may include proteins or nucleic acids.

The term "virtual stained image" (VSI) refers to an image of a biological sample that simulates that of an image obtained from a brightfield staining protocol. The image has similar contrast, intensity, and coloring as a brightfield image. This allows features within a biological sample, including but not limited to nuclei, epithelia, stroma or any type of extracellular matrix material features, to be characterized as if the brightfield staining protocol was used directly on the biological sample.

The invention includes embodiments that relate generally to methods applicable in analytical, diagnostic, or prognostic applications such as analyte detection, histochemistry, immunohistochemistry, or immunofluorescence. In some embodiments, the methods disclosed herein may be particularly applicable in histochemistry, immunostaining, immunohistochemistry, immunoassays, or immunofluorescence. In some embodiments, the methods disclosed herein may be particularly applicable in immunoblotting techniques, for example, western blots or immunoassays such as enzyme-linked immunosorbent assays (ELISA).

Methods for sequential staining and detecting multiple targets in a biological sample is described more fully in U.S. patent application Ser. No. 11/864,085 entitled "Sequential Analysis of Biological Samples", filed on Sep. 28, 2007 is incorporated herein by reference. Methods for co-localizing targets in a sample are described in U.S. patent application Ser. No. 11/686,649, entitled "System and Methods for Analyzing Images of Tissue Samples", filed on Mar. 15, 2007; U.S. patent application Ser. No. 11/500,028, entitled "System and Method for Co-Registering Multi-Channel Images of a Tissue Micro Array", filed on Aug. 7, 2006; U.S. patent application Ser. No. 11/606582, entitled "System and Methods for Scoring Images of a Tissue Micro Array, filed on Nov. 30, 2006, and U.S. application Ser. No. 11/680,063, entitled Automated Segmentation of Image Structures, filed on Feb. 28, 2007, each of which is herein incorporated by reference.

Methods to convert fluorescent images into a pseudo brightfield image are known. However, these methods typically reassign a specific color space (wavelength) to each fluorescent dye such that the fluorescent images are recolored into the brightfield space. These methods do not transpose the fluorescent images into an image that represents the image of the biological sample that would be obtained if the biological sample were subjected to a specified brightfield staining protocol, such as H&E. Also known is a method which creates a brightfield image from fluorescent images wherein structural features and details of the biological sample are identified as if the image was obtained directly from a specified brightfield staining protocol. The images that resemble the brightfield staining protocol may be referred to as a virtual stained image (VSI). Such a method is described in afore mentioned U.S. patent application Ser. No. 12/569396.

The disclosed invention describes a method to map a set of biomarker images acquired by a fluorescent microscope into a new color space where the mapped image intensity values represent a bright field modality and may be used to generate a VSI. The method involves using data acquired from corresponding points in two or more fluorescent images and a calibration function that is obtained from a bright-field image of a biological sample or defined using a preselected or desired color. The preselected or desired color may be chosen by an operator, which may be a pathologist or microscopist familiar with standard biological staining protocols. The calibration function estimates an intensity transformation that maps the fluorescent images into the brightfield color space using three parameters, a[Red], a[Green], a[Blue], called the "extinction coefficients.".

The estimated parameters may be derived by preparing one or more biological specimens with a wide range of staining intensity in the biomarker of interest, labeled with a visible dye such as hematoxylin, eosin, or diaminobenzidine (DAB). The sample may then be imaged in brightfield, and the distribution of red, green, and blue pixel intensity levels may be calculated; the pixel intensity levels are normalized to the interval [0,1]. The color with the smallest value for mean(log intensity) is identified. Without loss of generality, one may presume a specific color. For example, if the color is green, the mean values of (log Red/log Green) and (log Blue/log Green) are calculated, and the triple, (mean[ log Red/log Green], 1, mean[ log Blue/log Green]) are used as extinction coefficients.

In an alternative embodiment, the extinction coefficients may be derived without reference to an actual brightfield dye. Instead, a designer may choose a color that should be used for a moderately intense stain. If that color is (R, G, B) in a linear color model wherein the channels R, G, and B are normalized to the interval [0,1], then the extinction coefficients are simply (log R, log G, log B). This approach allows the method to simulate a bright-field stain using a dye that does not exist in nature.

The correspondence of the points in the fluorescent images may then be established by two methods: intensity-based and feature-based.

In a feature-based method, the image of the nuclei, epithelia, stroma or any type of extracellular matrix material is acquired for both the fluorescent image and the bright-field image. The featured-based structure may be selected using a manual process or automatically. Corresponding structures are selected in images from both modalities. For the fluorescent image, the image may be captured using a fluorescent microscope with an appropriate excitation energy source tuned to a given biomarker and with filters appropriate for collecting the emitted light. Similarly, multiple biomarkers can be imaged simultaneously without moving the sample under the microscope, or sequentially. As noted, the excitation wavelength and the filters can be changed for different markers. In certain embodiments, the microscope may be designed so that it can acquire both brightfield and fluorescent images. One such microscope may involve calibrated multiple optical paths and multiple cameras. A brightfield image of the sample may then be obtained which may then be segmented into Red (R), Green (G) and Blue (B) channels and the color and intensity of the feature-based structure measured.

In an intensity-based method, location of the sample area under the microscope may be controlled with electronic, magnetic, optical or mechanical sensors so that the sample area can be repeatedly located close to the same position for the next image acquisition. Intensity based registration is generally applicable to a broad class of biomarkers. Generally, the biological sample, which is fixed or otherwise provided on a substrate such as, but not limited to, a TMA, a slide, a well, or a grid, is labeled with molecular biomarkers, and imaged through a fluorescent microscope.

In one embodiment, a variety of molecular biomarkers may be used such as fluorescent dyes bound to antibodies or proteins. Then the sample is imaged under a fluorescent microscope using an excitation energy source that is tuned to the given biomarkers, and using various filters that are adapted to optimally collect the emitted light. Multiple biomarkers can be imaged simultaneously without moving the specimen under the microscope, or sequentially. For different biomarkers the excitation wavelength and the filters can be changed. Biomarkers may include, but are not limited to, the following list of markers which comprises a brief description of one or more but not necessarily all of the functions of each marker:

Her2/neu: epidermal growth factor over expressed in breast and stomach cancer, therapy by a monoclonal antibody slows tumor growth EGF-R/erbB: epidermal growth factor receptor ER: estrogen receptor required for growth of some breast cancer tumors, located in the nucleus and detected with ISH for deciding on therapy limiting estrogen in positive patients PR: progesterone receptor is a hormone that binds to DNA AR: androgen receptor is involved in androgen dependant tumor growth P53: tumor suppressor gene senses DNA damage; is inactivated in 50% of human cancer β-catenin: oncogene in cancer translocates from the cell membrane to the nucleus, which functions in both cell adhesion and as a latent gene regulatory protein Phospho-β-Catenin: phosphorylated form of β-catenin degrades in the cytosol and does not translocate to the nucleus GSK3β: glycogen synthase kinase-3β protein in the Wnt pathway phosphorylates β-catenin marking the phospo-β-catenin for rapid degradation in the protosomes PKCβ: mediator G-protein coupled receptor NFKβ: nuclear factor kappa B marker for inflammation when translocated to the nucleus Bcl-2: B cell lymphoma oncogene 2 acts as an apoptosis inhibitor CyclinD: cell cycle control VEGF: vascular endothelial growth factor related to angiogenesis E-cadherin: cell to cell interaction molecule expressed on epithelial cells, the function is lost in epithelial cancers c-met: tyrosine kinase receptor.

At least one additional fluorescent morphological marker that carries compartmental information may also be included in this step. This marker is chosen such that it carries common information with the next step and is used to register the images if sequential staining is involved. An area of the biological sample is then re-labeled with one or more morphological markers, which are visible in the brightfield color space, such as hematoxylin and eosin (H&E) dyes, and imaged again.

In some embodiments morphological markers may include, but are not limited to, the following:

Keratin: marker for epithelial cells

Pan-cadherin: marker for the cell membrane

Smooth muscle actin: marker for muscle

DAPI: marker for the nucleus

Hematoxylin marker for DNA (blue stain)

Eosin: marker for cytoplasm; depends on pH (red stain).

Some of these morphological markers can be imaged using a brightfield microscope, and some with fluorescent microscope. In any case, the morphological marker is chosen such that it has common information with the earlier step. For example if DAPI is used to image the nuclei in the earlier step, hematoxylin can be used to image the nuclei under a brightfield microscope in the second step. Since they both stain the same compartment, the images can be aligned by image registration techniques. DAPI a nuclear stain may be employed as the additional fluorescent morphological marker to register the nucleus stained with hematoxylin in the bright-field images with the fluorescent images. The images of the sample area are overlaid using both hardware and software registration techniques, and the information is stored whereby the technical effect is to register or otherwise produce multichannel images of the sample area.

An intensity-based method therefore allows both molecular and morphological markers to be imaged from the same biological sample using sequential imaging and co-registration techniques. Subsequently, the pixel intensity for given points on the area of the biological sample may be registered and compared for both the fluorescent images and the brightfield image. Similar to the feature-based method, the brightfield image is segmented into Red (R), Green (G) and Blue (B) channels.

In either the intensity-based or feature-based method, the transformation from the fluorescent images to the brightfield color space uses the estimated mapping parameter in a nonlinear transformation equation. The nonlinear transformation equation may be represented using the red, green, blue values or color space (R, G, B) and the transformation represented by the formulas:

$$R=255\exp(-a[Dye1]*z[Dye1]-a[Dye2]z[Dye2]-\ldots)$$

$$G=255\exp(-b[Dye1]*z[Dye1]-b[Dye2]z[Dye2]-\ldots)$$

$$B=255\exp(-c[Dye1]*z[Dye1]-c[Dye2]z[Dye2]-\ldots)$$

In the formulas, the scalars z[Dye1], z[Dye2], . . . are the fluorescent dye quantities observed at a given pixel location. The triples (a[Dyen], b[Dyen], c[Dyen]) are a constant times the extinction coefficients of the nth dye in the virtual stain as defined using a preselected or desired color. The constant is chosen so that the output color values (R, G, B) display a readable range of contrast in the image.

In one embodiment, the 0.995 quantiles are found for z[Dye1], z[Dye2], . . . , and the constants are chosen such that:

$$\min(\exp(-a[Dyen]*z[Dyen]),\exp(-b[Dyen]*z[Dyen]),\exp(-c[Dyen]*z[Dyen]))=1/255.$$

This embodiment causes the dynamic range of the output color to nearly fill the possible dynamic range of an 8-bit image, and results in an intense contrast.

A sharpening transform may be applied to the virtual stain image after it is synthesized. In one embodiment, the sharpening transform may be implemented as a linear convolution filter whose kernel is the matrix:

$$\begin{bmatrix} -0.25 & -0.25 & -0.25 \\ -0.25 & 3.00 & -0.25 \\ -0.25 & -0.25 & -0.25 \end{bmatrix}$$

Applying the sharpening transform gives the output image a crisper appearance with sharper edges and more visible fine details.

Once the transformation parameters are calculated, one or more selected areas of the sample may be used for transformation from a set of fluorescent images into a VSI using the virtual H&E mapping or a similar visual image such as brown DAB staining. The molecular biomarkers advantageously provide functional and compartmental information that is not visible using a brightfield image alone. For example, image analysis algorithms can benefit from the added channels to separate the sample compartments while still providing a pathologist or operator an image intensity values representative of a brightfield modality (H&E). For example, a VSI representative of a DAB staining protocol for keratin would show cell nuclei in shades of purple and the cytoskeleton of epithelial cells and fibroblasts in shades of brown.

In other embodiments, once the mapping parameters are estimated, the transformation algorithm may be applied to other fluorescent images to generate a VSI. The other fluorescent images may be from a different area of the same biological sample. For example, the source of the biological sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

In other embodiments, the other fluorescent images used to generate a VSI may be from a different biological sample. The different biological sample may include a collection of similar cells obtained from tissues of biological subjects that may have a similar function. Suitable examples of human tissues include, but are not limited to, (1) epithelium; (2) the connective tissues, including blood vessels, bone and cartilage; (3) muscle tissue; and (4) nerve tissue.

In some embodiments, a biological sample includes tissue sections from healthy or diseases tissue samples (e.g., tissue section from colon, breast tissue, and prostate). A tissue section may include a single part or piece of a tissue sample, for example, a thin slice of tissue or cells cut from a tissue sample. In some embodiments, multiple sections of tissue samples may be taken and subjected to analysis.

The methods disclosed herein may find applications in analytic, diagnostic, and therapeutic applications in biology and in medicine. In some embodiments, the methods disclosed herein may find applications in histochemistry, particularly, immunohistochemistry. Analysis of cell or tissue samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein, may facilitate accurate and reliable analysis of a plurality (e.g., potentially infinite number) of targets (e.g., disease markers) from the same biological sample.

In certain embodiments, the VSI generated may be used for pathological diagnostics and may further comprise the step of identifying one or more molecular pathways based on the molecular marker, wherein the molecular pathway is indicative of a disease. Although the methods may be used for a variety of diseases, one type for which the method is particularly suited is cancer including, but not limited to, epithelial cancers such as but not limited to breast, prostate and colon cancers.

In certain embodiments, the VSI generated may be used for quantitavie analysis comprising identifying molecular pathways as a function of one or more morphological structures selected from a group consisting of nuclei, epithelia, and stroma. For example, a stained fluorescent image may be transformed to an H&E coordinate system and viewed together to provide enhanced analysis.

An image analysis system for carrying out the method generally comprises: a means for at least temporarily storing the digital images stained with the molecular markers and the morphological stains in both the fluorecent and brightfield spaces; and a processor for co-registering the images using one or more registration if sequential staining is involved. The processor is also configured to calculate the mapping parameters by analyzing at least in part, featured based information or pixel intensity data information of the brightfield image and the two or more fluorescent images to transform the two or more fluorescent images into a VSI.

The system may further comprise a means for displaying one or more of the images; an interactive viewer; a virtual microscope; and/or a means for transmitting one or more of the images over a communications network. The processor may also superimpose one or more of the images with each other based, at least in part, on the segmentation of the morphological features.

In certain embodiments the processor is also configured to store mapping parameters from one or more previously analyzed biological samples. This provides a means for applying the transformation algorithm to other fluorescent images to generate a VSI. The other fluorescent images may be from a different area of the same biological sample or from different biological samples. The system may also allow the user to select from many available transformations and even adjust the transformation parameters interactively based on a visual inspection of the expected output (generated VSI).

In some embodiments, one or more of the aforementioned may be automated and may be performed using automated systems. In some embodiments, all the steps may be performed using automated systems.

EXAMPLES

Comparison of Virtual Stain with Actual DAB Staining for Cell Pellet Samples

Samples of fifteen human cell lines exhibiting different levels of expression were prepared by centrifugation of cells, immobilization of the cells in an agarose gel, formalin fixation and antigen retrieval. Serial sections of the cell pellets were then prepared using conventional immunoperoxidase +DAB staining and with a directly conjugated fluorescent antibody, with both antibodies being directed to the human epidermal growth factor receptor (EGFR). The DAB-stained specimen was counterstained with hematoxylin and imaged in color using a bright-field microscope. The immunofluorescent specimen was counterstained with DAPI and imaged in an automated fluorescence microscope in DAPI and in the wavelength of the fluorescent antibody.

The pixel intensities of the immunofluorescent image and the fluorescent image in the DAPI wavelength were both scaled linearly so that the mean pixel intensity returned by the detector when no incident light was applied was mapped to a value of 0.0 and the 0.995 quantile of the pixel intensity in all the images in a given wavelength was mapped to a value of 1.0. A VSI was then constructed using the formula:

$$R = 255 \exp[-0.8\, EGFR \log(255) - 0.6\, DAPI \log(255)]$$

$$G = 255 \exp[-1.0\, EGFR \log(255) - 1.0\, DAPI \log(255)]$$

$$B = 255 \exp[-1.428\, EGFR \log(255) - 0.34\, DAPI \log(255)]$$

where EGFR represents the scaled pixel intensity in the immunofluorescence wavelength, and DAPI represents the scaled pixel intensity in the DAPI wavelength.

Following this construction, the VSI was sharpened by applying a convolution filter with the kernel:

$$\begin{bmatrix} -0.25 & -0.25 & -0.25 \\ -0.25 & 3.00 & -0.25 \\ -0.25 & -0.25 & -0.25 \end{bmatrix}$$

Figure 1A:
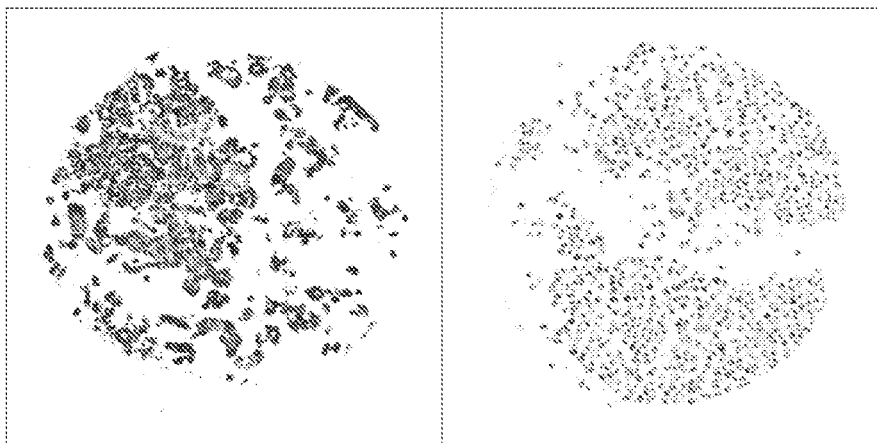
FIG. 1 shows a monochrome representation of the color image obtained from the bright field microscope of two representative cell pellets to which the DAB stain with hematoxylin counterstain was applied: (a) represents the red channel, (b) represents the green channel, and (c) represents the blue channel.
Figure 1B:
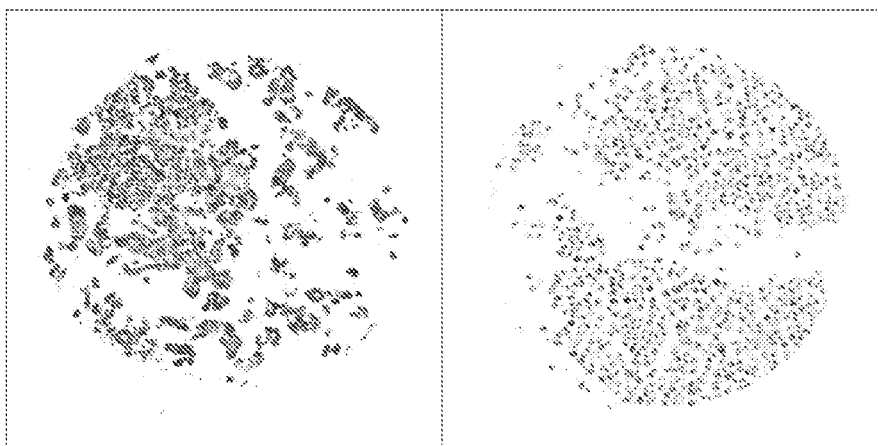
Figure 1C:
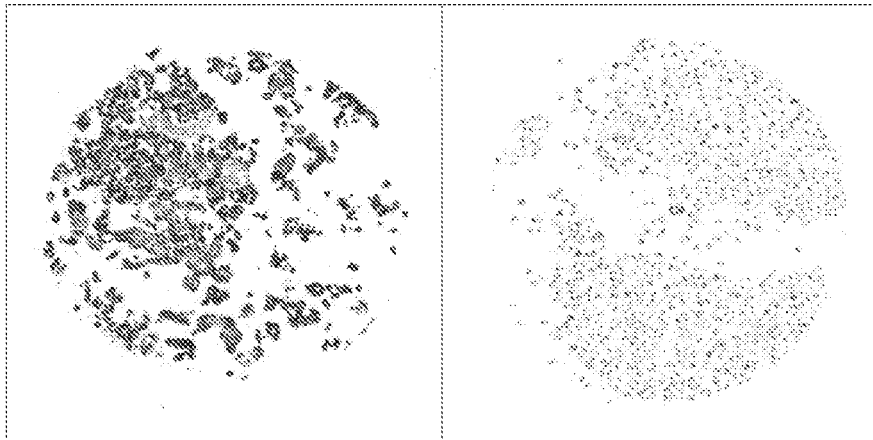

FIG. 1 shows a monochrome representation of the color image obtained from the bright field microscope of two representative cell pellets to which the DAB stain with hematoxylin counterstain was applied. As shown: (a) represents the red channel, (b) represents the green channel, and (c) represents the blue channel. The pellet on the left stains strongly express for the EGFR antigen; the one on the right stains weakly or not at all (negative for EGFR). The fluorescence and virtual-stained images are both derived from the same images on the microscope.

Figure 2A:
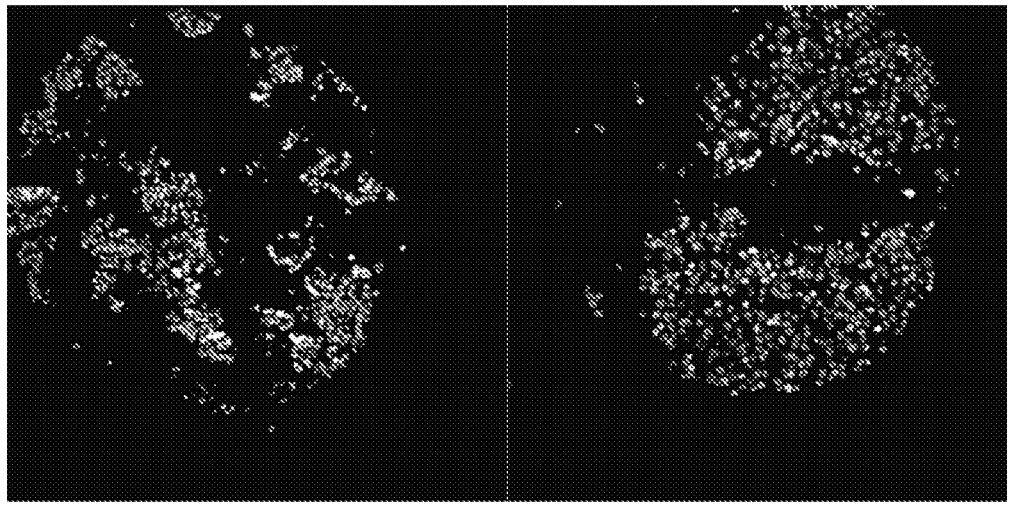
FIG. 2 shows monochrome fluorescence images of the immunostained specimens obtained from the fluorescence microscope. Image (a) represents the fluorescence intensity in the DAPI wavelength, which preferentially labels cell nuclei, and (b) represents the fluorescence intensity in the wavelength emitted by the conjugated antibody, which labels the epidermal growth factor receptor.
Figure 2B:
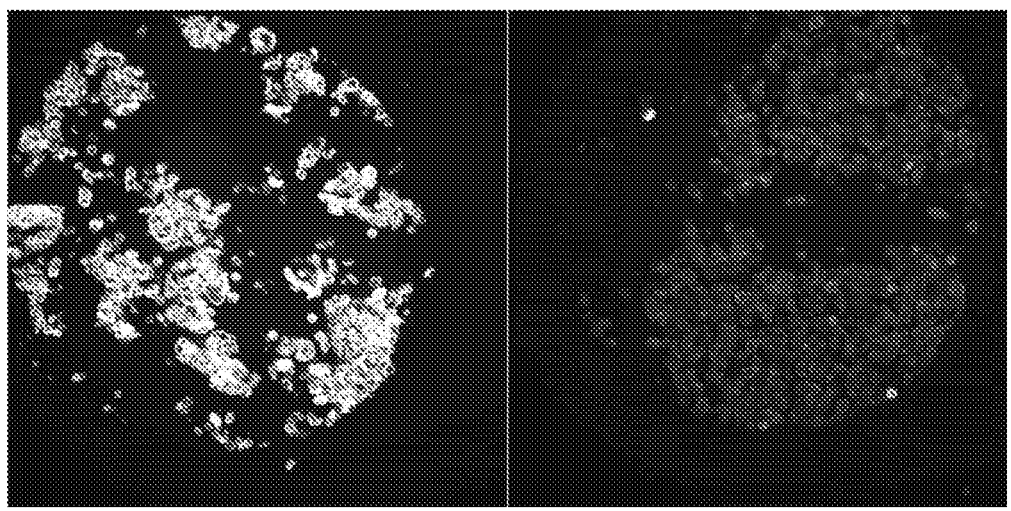

FIG. 2 shows monochrome fluorescence images of the immunostained specimens obtained from the fluorescence microscope. Image (a) represents the fluorescence intensity in the DAPI wavelength, which preferentially labels cell nuclei, and (b) represents the fluorescence intensity in the wavelength emitted by the conjugated antibody, which labels the epidermal growth factor receptor.

FIG. 3 shows a monochrome representation of the color VSI obtained by processing the fluorescence images according to the method taught herein. Image (a) represents the red channel; (b) represents the green channel; and (c) represents the blue channel. The cells in the field of view are obtained from the same pellets as the images in FIG. 1. The pellet on the left stains strongly positive for the EGFR antigen, while the one on the right stains weakly or not at all. The staining pattern in FIG. 3 can be observed to show the same cellular features as that in FIG. 1, but with greater definition of fine detail. It displays exactly the same information as shown in FIG. 2, but in a form that is easier for the human eye to interpret.

These methods merge molecular pathology and standard anatomical pathology. H&E based staining is the most common brightfield microscopy staining technique used in standard pathology. As described above, hematoxylin stains cell nuclei blue, while, as a counter-stain, eosin stains cytoplasm and connective tissue pink. There are a great number of other known stain combinations that can be used as alternative staining for brightfield microscopy. For example, Feulgen staining can be used to image nucleic acids, or Orcein can be used to image connective tissue fibers.

These multi-channel methods are not limited to morphological stains or fluorescent biomarkers or even to pathology. Any stain that enables some informative aspect or feature of a biological sample to be visualized so that it can be digitally imaged and processed would be suitable for these methods. Suitable stains include, but are not necessarily limited to, cytological or morphological stains, immunological stains such as immunohisto- and immunocyto- chemistry stains, cytogenetical stains, in situ hybridization stains, cytochemical stains, DNA and chromosome markers, and substrate binding assay stains. Other medical and bioscience applications can benefit from the extended multi-channels. These multi-channel methods provide a flexible framework in which markers can be imaged sequentially without being limited to optical, chemical, and biological interactions.

While only certain features of the invention have been illustrated and described herein, many modifications and changes will occur to those skilled in the art. It is, therefore, to be understood that the appended claims are intended to cover all such modifications and changes as fall within the scope and spirit of the invention.

I claim:

1. A method for generating a brightfield type image that resembles a brightfield staining protocol comprising the steps of:
    acquiring image data of two or more fluorescent images of a fixed area on a biological sample;
    analyzing the image data utilizing, at least in part, featured based information or pixel intensity data information to generate mapping parameters wherein said mapping parameters comprises a nonlinear estimation model;

applying said mapping parameters to the fluorescent images;
transforming the two or more fluorescent imaging into a brightfield color space; and
generating a brightfield type image.
where the nonlinear estimation model is defined as:

$$R = 255 \exp(-a[\text{Dye1}]*z[\text{Dye1}] - a[\text{Dye2}]z[\text{Dye2}] - \ldots a[\text{Dyen}]z[\text{Dyen}])$$

$$G = 255 \exp(-b[\text{Dye1}]*z[\text{Dye1}] - b[\text{Dye2}]z[\text{Dye2}] - \ldots)$$

$$B = 255 \exp(-c[\text{Dye1}]*z[\text{Dye1}] - c[\text{Dye2}]z[\text{Dye2}] - \ldots)$$

wherein R, G, and B are resulting red, green and blue pixel values in the brightfield type image;
z is a scaling coefficient for a fluorescent dye quantities observed at a given pixel location; and
a, b, and c are the extinction coefficients corresponding to the brightfield color space, and wherein the triples, a[Dyen], b[Dyen], c[Dyen], are a constant times the extinction coefficients of the nth dye in the virtual stain as defined using a preselected or desired color.

2. The method of claim 1 wherein the constants [Dyen] are chosen such that:

$$\min(\exp(-a[\text{Dyen}]*z[\text{Dyen}]), \exp(-b[\text{Dyen}]*z[\text{Dyen}]), \exp(-c[\text{Dyen}]*z[\text{Dyen}])) = 1/255.$$

3. The method of claim 1 further comprising applying a sharpening transformation correction to the brightfield type image.

4. The method of claim 3 wherein said sharpening transformation correction comprising a convolution filter whose kernel is the matrix:

$$\begin{bmatrix} -0.25 & -0.25 & -0.25 \\ -0.25 & 3.00 & -0.25 \\ -0.25 & -0.25 & -0.25 \end{bmatrix}.$$

5. The method of claim 1 wherein the brightfield type image corresponds to an immunostained type image having a red, green, and blue three channel color space.

6. The method of claim 1 wherein at least one image of the two or more fluorescent images is of autofluorescence.

7. The method of claim 1 wherein the acquiring a brightfield image step comprises the steps of sequentially staining the biological sample with two or more histochemical or immunohistochemical stains.

8. The method of claim 1 wherein the feature based information comprises one or more features selected from a group consisting of nuclei, epithelia, and stroma.

9. The method of claim 1 further comprising the step of applying the mapping parameters to two or more fluorescent images of a second fixed area wherein the second fixed area is from the same or a different biological sample.

10. The method of claim 1 further comprising the step of pathological diagnostics using said brightfield type image.

11. The method of claim 10 wherein the pathological diagnostics is for cancer.

12. The method of claim 1 further comprising the step of quantitative analysis using said brightfield type image.

13. The method of claim 12 wherein the step of quantitative analysis comprises identifying molecular pathways as a function of one or more morphological structures selected from a group consisting of nuclei, epithelia, and stroma.

14. An image analysis system for generating a brightfield type image that resembles a brightfield staining protocol of a biological sample, using fluorescent images comprising:
a digital imaging device adapted to acquire two or more fluorescent images of a fixed area on a biological sample;
a processing device configured to;
analyzing the image data utilizing, at least in part, featured based information or pixel intensity data information to generate mapping parameters wherein said mapping parameters comprises a nonliner estimation model;
applying said mapping parameters to the fluorescent images;
transforming the two or more fluorescent imaging into a brightfield color space; and
generating a brightfield type image; and
a display device for displaying said brightfield image;
where the nonlinear estimation model is defined as:

$$R = 255 \exp(-a[\text{Dye1}]*z[\text{Dye1}] - a[\text{Dye2}]z[\text{Dye2}] - \ldots a[\text{Dyen}]z[\text{Dyen}])$$

$$G = 255 \exp(-b[\text{Dye1}]*z[\text{Dye1}] - b[\text{Dye2}]z[\text{Dye2}] - \ldots)$$

$$B = 255 \exp(-c[\text{Dye1}]*z[\text{Dye1}] - c[\text{Dye2}]z[\text{Dye2}] - \ldots)$$

wherein R, G, and B are resulting red, green and blue pixel values in the brightfield type image.
z is a scaling coefficient for a fluorescent dye quantities observed at a given pixel location; and
a, b, and c are the extinction coefficients corresponding to the brightfield color space, and wherein the triples, a[Dyen], b[Dyen], c[Dyen], are a constant times the extinction coefficients of the nth dye in the virtual stain as defined using a preselected or desired color.

15. The system of claim 14 wherein the constants [Dyen] are chosen such that:

$$\min(\exp(-a[\text{Dyen}]*z[\text{Dyen}]), \exp(-b[\text{Dyen}]*z[\text{Dyen}]), \exp(-c[\text{Dyen}]*z[\text{Dyen}])) = 1/255.$$

16. The system of claim 14 further comprising applying a sharpening transformation correction to the brightfield type image.

17. The system of claim 16 wherein said sharpening transformation correction comprising a convolution filter whose kernel is the matrix:

$$\begin{bmatrix} -0.25 & -0.25 & -0.25 \\ -0.25 & 3.00 & -0.25 \\ -0.25 & -0.25 & -0.25 \end{bmatrix}.$$

18. The system of claim 14 wherein the processing device is further configured to store mapping parameters from one or more previously analyzed biological samples.

* * * * *

UNITED STATES PATENT AND TRADEMARK OFFICE
CERTIFICATE OF CORRECTION

PATENT NO. : 8,639,013 B2  
APPLICATION NO. : 13/211725  
DATED : January 28, 2014  
INVENTOR(S) : Kenny Page 1 of 1

It is certified that error appears in the above-identified patent and that said Letters Patent is hereby corrected as shown below:

In the Claims

Column 13, Line 5, in Claim 1, delete "image." and insert -- image; --, therefor.

Column 13, Line 6, in Claim 1, delete "where" and insert -- wherein --, therefor.

Column 14, Line 15, in Claim 14, delete "nonliner" and insert -- nonlinear --, therefor.

Column 14, Line 22, in Claim 14, delete "where" and insert -- wherein --, therefor.

Column 14, Line 33, in Claim 14, delete "image." and insert -- image; --, therefor.

Signed and Sealed this  
Twenty-seventh Day of May, 2014

Michelle K. Lee  
*Deputy Director of the United States Patent and Trademark Office*